(12) United States Patent
Hopper et al.

(10) Patent No.: US 9,909,926 B2
(45) Date of Patent: Mar. 6, 2018

(54) CHEMICAL SENSOR

(71) Applicant: AMS Sensors UK Limited, Cambridge, Cambridgeshire (GB)

(72) Inventors: Richard Henry Hopper, Cambridge (GB); Andrea De Luca, Cambridge (GB); Kaspars Ledins, Cambridge (GB); Syed Zeeshan Ali, Cambridge (GB); Mohamed Foysol Chowdhury, Milton (GB)

(73) Assignee: AMS SENSORS UK LIMITED (GB)

( * ) Notice: Subject to any disclaimer, the term of this patent is extended or adjusted under 35 U.S.C. 154(b) by 0 days.

(21) Appl. No.: 15/168,562

(22) Filed: May 31, 2016

(65) Prior Publication Data
US 2017/0343419 A1 Nov. 30, 2017

(51) Int. Cl.
*G01J 5/14* (2006.01)
*G01N 21/61* (2006.01)
(Continued)

(52) U.S. Cl.
CPC .............. *G01J 5/14* (2013.01); *B01L 3/50273* (2013.01); *B01L 3/502707* (2013.01);
(Continued)

(58) Field of Classification Search
CPC ........ G01J 5/06; G01J 5/16; G01J 5/20; G01J 5/14; G01N 21/552; G01N 21/61; H01L 31/02002
See application file for complete search history.

(56) References Cited

U.S. PATENT DOCUMENTS 5,834,777 A 11/1998 Wong
RE36,277 E 8/1999 Black et al.
(Continued)

FOREIGN PATENT DOCUMENTS

| EP | 2743677 | 6/2014 |
|---|---|---|
| KR | 20090004274 | 1/2009 |
| WO | 20130167874 | 11/2013 |

OTHER PUBLICATIONS

Andreas Pusch et al., "A highly efficient CMOS nanoplasmonic crystal enhanced slow-wave thermal emitter improves infrared gas-sensing devices", Scientific Reports, vol. 5, Dec. 7, 2015, p. 17451.

(Continued)

*Primary Examiner* — David Porta
*Assistant Examiner* — Faye Boosalis
(74) *Attorney, Agent, or Firm* — Tarolli, Sundheim, Covell & Tummino LLP

(57) ABSTRACT

We disclose a chemical sensing device for detecting a fluid. The sensing device comprises: at least one substrate region comprising at least one etched portion; a dielectric region formed on the at least one substrate region, the dielectric region comprising at least one dielectric membrane region adjacent to the at least one etched portion; an optical source for emitting an infra-red (IR) signal; an optical detector for detecting the IR signal emitted from the optical source; one or more further substrates formed on or under the dielectric region, said one or more further substrates defining an optical path for the IR signal to propagate from the optical source to the optical detector. At least one of the optical source and optical detector is formed in or on the dielectric membrane region.

30 Claims, 14 Drawing Sheets

(51) Int. Cl.

| | | |
|---|---|---|
| *G01N 33/00* | (2006.01) | |
| *B01L 3/00* | (2006.01) | |
| *G01N 21/552* | (2014.01) | |
| *H01L 31/16* | (2006.01) | |
| *H01L 31/0232* | (2014.01) | |
| *H01L 31/02* | (2006.01) | |
| *H01L 35/32* | (2006.01) | |
| *H01L 37/00* | (2006.01) | |
| *H01L 31/167* | (2006.01) | |
| *H01L 31/0203* | (2014.01) | |
| *H01L 31/18* | (2006.01) | |

(52) U.S. Cl.
CPC ...... *B01L 3/502715* (2013.01); *G01N 21/552* (2013.01); *G01N 21/61* (2013.01); *G01N 33/004* (2013.01); *H01L 31/02002* (2013.01); *H01L 31/0203* (2013.01); *H01L 31/02325* (2013.01); *H01L 31/16* (2013.01); *H01L 31/167* (2013.01); *H01L 31/18* (2013.01); *H01L 35/32* (2013.01); *H01L 37/00* (2013.01); *B01L 2200/12* (2013.01); *B01L 2300/0654* (2013.01); *B01L 2300/08* (2013.01); *B01L 2300/0858* (2013.01); *B01L 2300/0887* (2013.01); *B01L 2300/168* (2013.01); *B01L 2400/0424* (2013.01); *G01N 2201/068* (2013.01)

(56) References Cited

U.S. PATENT DOCUMENTS

| | | |
|---|---|---|
| 6,469,303 B1 | 10/2002 | Sun et al. |
| 6,753,967 B2 | 6/2004 | Stuttard |
| 7,449,694 B2 | 11/2008 | Yi et al. |
| 7,609,375 B2 | 10/2009 | Park |
| 8,471,208 B1 | 6/2013 | Tang |
| 9,214,604 B2 | 12/2015 | Ali et al. |
| 2005/0161605 A1 | 7/2005 | Yokura et al. |
| 2007/0018077 A1* | 1/2007 | Puscasu ............... G01J 1/42 250/210 |
| 2008/0035848 A1 | 2/2008 | Wong |

OTHER PUBLICATIONS

Udrea F. et al., "SOI sensing technologies for harsh environment", Semiconductor Conference (CAS), Oct. 15, 2012, pp. 3-10.
International Search Report and Written Opinion dated Sep. 19, 2017 for corresponding International application No. PCT/GB2017/051467.

* cited by examiner

CHEMICAL SENSOR

FIELD OF THE INVENTION

The invention relates to a miniature chemical sensor based on the principle of infrared detection.

BACKGROUND OF THE INVENTION

Optical sensor technology can be used to detect a large range of chemicals including $CO_2$, CO, $NO_2$, VOCs and alcohol. For example Nondispersive infrared (NDIR) type sensor systems can offer good sensitivity, stability and selectivity. They have many applications, including ambient air quality and safety monitoring. Similarly Attenuated Total Reflection (ATR) systems also use IR radiation to determine the composition of a chemical.

Infrared gas sensors exploit the principle of optical absorption. When infrared radiation passes through a gas, some of the optical energy is absorbed and transitions occur between the vibrational-rotational energy levels within the gas molecules. This process creates 'absorption lines' in the mid infrared spectrum (generally between 2.5-16 µm). The characteristics of the absorption spectra depend on the number and masses of atoms in the molecules, as well as the nature of the various chemical bonds. A commonly detected gas is carbon dioxide ($CO_2$) which has strong absorption lines at a wavelength of 4.26 µm.

A basic single channel NDIR system consists of a broadband infrared source which emits infrared radiation through a gas cell. An optical bandpass filter is used to select the absorption wavelength of interest and an infrared detector detects the transmitted IR signal. When the target gas concentration is low, there is limited interaction between the optical signal and the gas molecules and the detected signal is therefore high. If the target gas is introduced, optical absorption occurs and the detected signal level drops in proportion to the gas concentration. The transmitted optical intensity is described by the Lambert and Beer law $$I = I_0 e^{-kcl}$$

where $I_0$ is the initial intensity, k is the gas specific absorption coefficient, c is the gas concentration and l is the length of the optical absorption path.

The infrared source used for the system can be a broadband thermal emitter such as an MEMS infrared source, infrared incandescent lamp or blackbody radiation source. Alternatively, a narrow band source, such as an infrared diode or laser can be used. The choice depends on a number of factors, including the optical power, spectral characteristics, cost and frequency response. Typically, micro-bulbs are used which have the advantage of being extremely cheap and provide good emission at short mid-IR wavelengths. Disadvantages are that they have high power consumption, are bulky, and have limited emission at longer wavelengths (>5 µm) due to optical absorption by the glass envelope. As a result, MEMS IR emitters are increasingly being used which consist of a micro-heater embedded within a membrane that is thermally isolated from a silicon substrate. These can offer good performance across a broader range of wavelengths and better integration with other chip based technology.

Two types of IR detector are available: thermal and quantum detectors. Thermal detectors respond to the heating of a material and include: bolometers, thermopile and pyroelectric detectors. They typically have a broadband response in the mid IR waveband and have to be used with optical filters for gas sensing applications. Quantum type detectors, such as photodiodes and photoconductive sensors, are fabricated from semiconductor materials which determine their spectral response. For most optical gas sensing applications, thermal detectors are used as they give adequate performance, do not require cooling, are lower cost, and can be integrated on a semiconductor chip.

In a refinement of the basic NDIR approach described, a dual channel system can be used to help compensate for the effect of system drift, for example, due to variations in IR emission from the source over time. With this approach, a second 'reference' detector is used with a detection wavelength well away from the absorption wavelength of the target gas. Often dual channel detectors are integrated within the metal package of a single component.

A number of NDIR sensor designs are known, for example U.S. RE36277, U.S. Pat. No. 8,471,208, US 20080035848, U.S. Pat. No. 7,449,694, U.S. Pat. No. 6,469,303, U.S. Pat. No. 6,753,967 and U.S. Pat. No. 7,609,375. However, they all require an optical assembly which cannot be easily integrated with existing semiconductor chip technology. This precludes their use in many applications where a small form factor is required, such as for mobile phones.

In U.S. Pat. No. 5,834,777, Wong discloses a miniature NDIR gas sensor made in semiconductor technology which results in a small size, even including the optical path. In this design there is a substrate with both an IR emitter and IR detector, and a second substrate which is etched to form an optical path, and the two substrates joined together to form an optical waveguide. A diffusion type gas sample chamber is formed within the waveguide and interposed in the optical path between the light source and the light detector. However the device has a large bulk-etched substrate portion below and above the optical path. Because of its closeness to the IR emitters and detectors, it is not possible to have these on a dielectric membrane. As a result the emitter has to be either a photodiode—which has low emission and stability issues, or can be a heater but with a high power consumption. Similarly the IR detector cannot be on a membrane, and so has much lower sensitivity.

SUMMARY

According to one aspect of the present invention, there is provided a chemical sensing device for detecting a fluid, the sensing device comprising:
  at least one substrate region comprising at least one etched portion;
  a dielectric region formed on the at least one substrate region, wherein the dielectric region comprises at least one dielectric membrane region adjacent to the at least one etched portion;
  an optical source for emitting an infra-red (IR) signal;
  an optical detector for detecting the IR signal emitted from the optical source;
  one or more further substrates formed on or under the dielectric region, wherein said one or more further substrates define an optical path for the IR signal to propagate from the optical source to the optical detector; and
  wherein at least one of the optical source and optical detector is formed at least partially in or on the dielectric membrane region.

The dielectric membrane region is immediately adjacent to the etched portion of the substrate region. In other words, the dielectric membrane region is the area in the dielectric region which is immediately above or adjacent to the etched portion of the substrate. The dielectric membrane region is a sub-set of the dielectric region, the sub-set being the immediately above or adjacent portion of the etched portion of the substrate region. The optical source (or the IR emitter) and/or the optical detector (or the IR detector) are at least partially or fully inside the dielectric membrane region.

The at least one substrate region may comprise a first etched portion and a second etched portion, and the dielectric region may comprise a first dielectric membrane region adjacent to the first etched portion and a second dielectric membrane region adjacent to the second etched portion, and the optical source may be located within the first dielectric membrane region and the optical detector is located within the second dielectric membrane region. The optical source and optical detector are laterally spaced to one another. In this embodiment, the substrate region includes two etched portions and two dielectric membranes. The optical source and detector are located in the separate dielectric membrane region. In an alternative embodiment, the substrate region may have only one etched portion and one dielectric membrane region. In such a case, the optical source and detector may be both located in the same dielectric membrane region. Alternately, only one of the optical source or detector may be on a dielectric membrane while the other is not on a dielectric membrane, but on the substrate or dielectric region. It would be appreciated that the further substrates can be located both above or below the dielectric region. For example, the further substrates can be located below the main semiconductor substrate region on which the dielectric membrane region is formed. In such an embodiment, a further dielectric region is provided between the main semiconductor substrate region and the further substrates and the further dielectric region is below or underneath the main semiconductor substrate region.

The at least one substrate region may comprise a first substrate and a second substrate. The first substrate may comprise a first etched portion and a first dielectric membrane region may be formed adjacent to the first etched portion. The second substrate may comprise a second etched portion and a second dielectric membrane region may be formed adjacent to the second etched portion. The optical source may be located within the first dielectric membrane region and the optical detector may be located within the second dielectric membrane region. The optical source and the optical detector may be vertically spaced to one another and the one or more further substrates may be vertically spaced between the first and second dielectric membrane regions. In this embodiment, the substrate region may include two separate substrates, which are the first and second substrates. Each of the first and second substrates may include separate etched portions and therefore the corresponding dielectric regions may include separate dielectric membrane regions. These vertically spaced substrates may be vertically spaced to one another.

According to a further aspect of the present invention, there is provided a method of manufacturing a chemical sensing device for detecting a fluid, the method comprising:
forming at least one substrate region;
depositing a dielectric region on the at least one substrate region, wherein the dielectric region comprises at least one dielectric membrane region adjacent to the at least one etched portion;
forming an optical source for emitting an infra-red (IR) signal;
forming an optical detector for detecting the IR signal emitted from the optical source;
etching the at least one substrate region to form an etched portion in the substrate region and at least one dielectric membrane region in the dielectric region, the at least one dielectric membrane region being adjacent to the etched portion;
forming one or more further substrates on or under the dielectric region, wherein said one or more further substrates define an optical path for the IR signal to propagate from the optical source to the optical detector; and
wherein at least one of the optical source and optical detector is formed in or on the dielectric membrane region.

The optical path, through which infrared radiation propagates, may be formed by one or more cavities (chamber) in one or more stacked substrate layers (further substrates). If a semiconductor substrate layer is used, the cavity may be created using a semiconductor etching process, including wet and dry etching. Wet etching processes may include: Potassium Hydroxide (KOH), Tetramethylammonium Hydroxide (TMAH) and Ethylene Diamine Pyrochatechol (EDP) etching. Dry etching processes may include reactive ion etching (RIE), Deep Reactive-Ion Etching (DRIE), sputter etching, and vapour phase etching. A mask (a photoresist or physical mask) may be used for patterning.

The optical path may also be formed of through silicon vias (TSVs), for example, a stack of multiple substrates between an IR emitter and an IR detector, with the multiple substrates having TSVs to allow IR radiation to reach the detector. The optical path may also be a combination of TSVs and bulk etched substrates The optical path created by the cavity may be used to channel optical radiation between the source and detector and through the chemical. A reflective layer(s) on the walls of the cavity may be used to reduce optical losses and may take the form of a metalised layer. Reflective materials may include gold, aluminium, copper, silver and/or platinum which may be deposited using a standard semiconductor deposition process such as physical vapour deposition (PVD) or CVD (Chemical Vapour Deposition). There may also be one or more additional layers between the substrate and the reflective materials to improve adhesion.

To optimise the length of the optical path, the cavity may be made in different shapes through one or more substrate layers, for example, a spiral, meander, or any other geometric pattern which would allow optical radiation to propagate from the emitter to the detector either directly or through reflections. Optical cavities may also be created in multiple stacked substrate layers through which IR radiation may propagate. The use of multiple cavities in separate substrate layers may allow an extension to the path length to be achieved within a small lateral size.

Different structures may be used to enhance the optical coupling of IR radiation between the source, detector and cavity, or between different cavities in one or more substrate layers may be provided. This may take the form of one or more reflectors, formed by the walls of the cavity and used to channel/direct radiation. If a semiconductor material such as silicon is used as a substrate material for the cavity, sloped or curved side walls may be created as a result of an anisotropic, or isotropic wet etching process. Additionally, side walls of various shapes may also be created by a dry etching process such as reactive ion etching (RIE) by controlling the anisotropy of the etching process, and changing the balance between the chemical (isotropic) etch and physical (anisotropic) etching.

One or more hollow channels may be provided into and out of the cavity to allow the flow of gas from the external environment. Openings in the cavity may be created by etching channels in one or more of the substrate layers. An opening for gas flow may also be created between substrate layers by spacing the layers apart. Spacers may take the form of ball bonds. Gas flow into and out of the cavity may occur due to diffusion or the forced movement of molecules.

In another embodiment of the invention, the approach may be used to sense liquids, composition of a liquid, or contaminants in a liquid, including water, bodily fluids and industrial solutions. In this case, the optical cavity and any connecting channels may be filled with a liquid rather than a gas. The liquid may fill the entire optical path, or only part of the path. The liquid may also cover a substrate layer and interact with an evanescent wave that extends beyond the surface of the substrate into the sample (Attenuated Total Reflectance (ATR) type method). This approach may be used to sense molecules in a sample which absorb infrared energy, as the propagating wave will be attenuated or spectrally altered. The top surface of the ATR system may have plasmonic layers (or the patterned structures).

The substrate layers may be bonded together. Bonding may be achieved in a number of ways, including through the use of solder pads, bump bonding, adhesive bonding, thermo-compression, direct bonding, wafer bonding and hybrid methods. Through-silicon vias (TSVs) may be used to form vertical electrical connections, passing through one or more substrate layers, and also to provide an electrical connection from the NDIR sensor to an external system, for example on a PCB.

Additional circuitry may be incorporated in any one of the layers and may include amplifiers to amplify the detected signal, multiplexing to read multiple detector elements, analogue to digital convertors for digitisation, MOSFET/transistor switches for driving the IR source, ASIC and microprocessor units for control and signal processing.

The substrate stack may incorporate different CMOS technology nodes, optimized for functionality. For example, the IR source and detector may be created using a 1 µm semiconductor process technology and circuitry may be created on a separate substrate using a finer process e.g. 180 nm.

The IR source is fabricated using a semiconductor process. This may take the form of a MEMS thermal source, formed by an electrically resistive heater, supported by a membrane formed by a dielectric material such as $SiO_2$ or SiN. The heating element may take the form of a metallised track (e.g. tungsten, titanium, copper, platinum and/or gold), an electrically resistive semiconductor layer, or a bipolar transistor or MOSFET. The device can be made in a CMOS process or a non-CMOS process. The IR source may also take the form of a quantum source e.g. an LED (e.g. an InAs, InSb and HgCdTe based LED) or LASER.

The IR detector is fabricated using a semiconductor process. The detector may take the form of a thermal detector such as a thermopile, bolometer or pyroelectric detector. One approach would be to use a thermopile detector, fabricated using one or more thermoelectric materials, including n or p doped poly/mono crystalline silicon, geranium, or a metal such as bismuth, antimony, aluminium, platinum, nickel, gold, tungsten and/or titanium. A CMOS process may be used for fabrication. The detector may also take the form of a quantum type detector such as a photodiode or photoconductive detector.

The IR emitter and/or IR detector may be fabricated on a dielectric membrane. The membrane materials may consist of silicon dioxide and/or silicon nitride. The membrane may be formed by back-etching of a substrate using wet or dry etching. The walls of the membrane trench can be sloping or near vertical. The membrane can be a full closed membrane, supported along its entire perimeter. Alternately it may only be supported by two or more beams—such a structure can be formed by front etching of a substrate.

The IR source and detector may be fabricated on a single substrate/chip or separate substrates. The substrates may be abutted or spaced apart at any distance. The use of separate substrates may facilitate the use of different fabrication processes and improve thermal isolation between components e.g. the thermal source and detector. In case of separate substrates, the substrates can also be one on top of the other, or may have one or more substrate between them.

A method to control the spectra of the detected IR radiation may be provided. This may either take the form of a narrow band emitter/absorber or a discrete optical filter. In one approach, a plasmonic structure (or the patterned structures) may be integrated with a thermal IR detector and/or emitter and designed to emit and/or absorb radiation at the absorption wavelength of the target gas. A plasmonic structure may be fabricated using a geometric pattern, for example, an array of holes and dots in a metal or semiconductor layer of a thermal source/detector. The plasmonic structure maybe made using a CMOS metal such as titanium, tungsten, copper, aluminium, or a non-CMOS metal such as platinum or gold, or using polysilicon or single crystal silicon. There maybe one or more layer with plasmonic structures. It is also possible to make a plasmonic structure by creating holes within the dielectric layers of the membrane.

In a further approach, a conventional optical filter may be used to control the spectra of the detected IR radiation. This may take the form of a bandpass filter used to pass IR radiation at the absorption wavelength of a gas. The optical filter may be stacked between substrate layers. It may take the form of a filter/window on a dielectric membrane supported by a substrate.

Multiple IR sources, detectors or filters with different spectral responses may be used. This arrangement may be used to sense multiple gas types or mixtures of gases e.g. to discriminate between volatile organic compounds, or mixture of carbon dioxide and alcohol vapour. In one approach, multiple spectral responses may be achieved using an IR source or detector array with integrated plasmonic structures to emit/absorb radiation at different optical wavelengths. In another approach, multiple optical filters may be used, e.g. multiple bandpass filters fabricated on one or more substrate layers.

In a further embodiment of the invention, different optical path lengths may be created between IR source and detector components, for example, to optimise the sensing of different gas types or concentrations of gas. Feeder cavities at different points off the main cavity may be used to illuminate different IR detectors. Alternatively, fully separate optical paths and IR source-detector pairs may be used. Furthermore, an IR detector for sensing at a reference wavelength (unaffected by the target gas) may be located in close proximity to the IR source.

The NDIR gas sensor may be packaged in a number forms, including in SMD, TO, ceramic, dual-in-line or any other type of semiconductor package. The substrates may be attached to the package using solder pads, bump bonding, adhesive bonding, thermo-compression, direct bonding and hybrid methods. Through-silicon vias (TSVs) or wire bonds may be used to form electrical connections to the package.

The device may have numerous applications, including environmental air quality monitoring and gas leak detection. The small form factor of the sensor permits use in mobile consumer devices including mobile phones, tablet computers and PDAs.

The sensor may also be used to control air ventilation units (HVAC systems) in buildings and vehicles.

BRIEF DESCRIPTION OF THE PREFERRED EMBODIMENTS

Some preferred embodiments of the invention will now be described by way of example only and with reference to the accompanying drawings, in which:

FIG. 15($b$) shows top view of the embodiment of the ring structures that overlaps the etched and un-etched parts of the substrate;

DETAILED DESCRIPTION OF THE PREFERRED EMBODIMENTS

Figure 1:
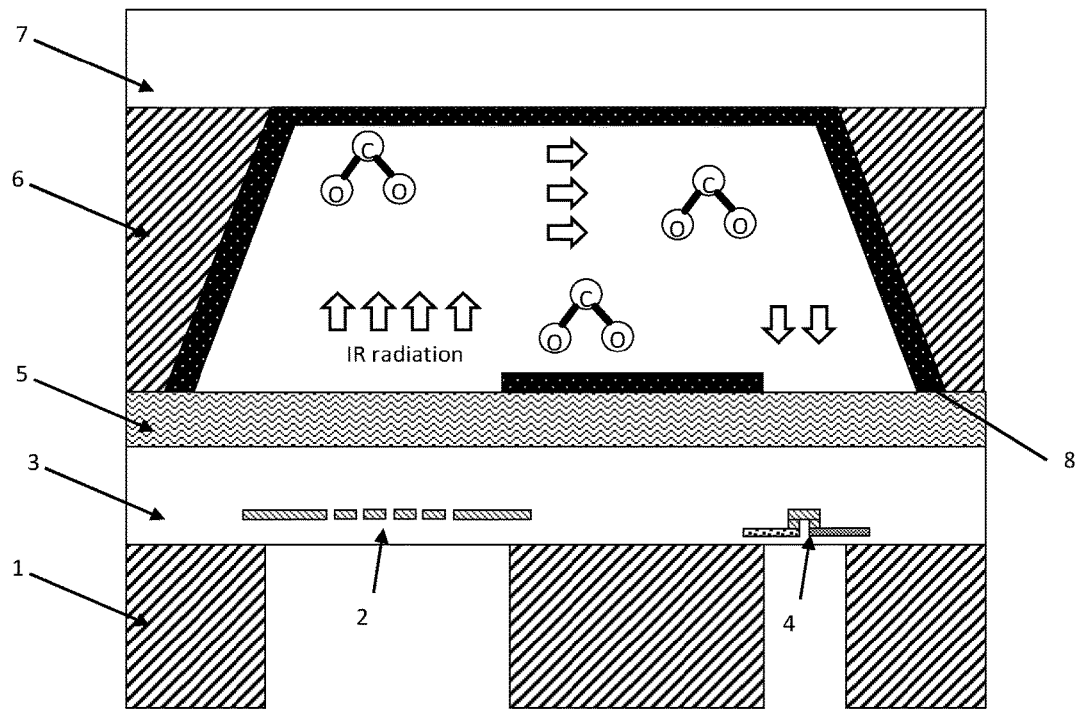
FIG. 1 is a cross sectional view of a chip level NDIR chemical sensor.

FIG. 1 shows the cross-section of a chemical sensing device, comprising an IR source and an IR detector fabricated on the same semiconductor substrate 1. The IR source is in form of an electrically resistive heater 2, embedded within a membrane formed by etching the semiconductor substrate 1. The dielectric layer 3 acts as etch-stop. The IR detector is in form of a thermopile 4, embedded within a membrane formed by etching the semiconductor substrate 1. The dielectric layer 3 acts as etch-stop. The chemical sensing device further comprises an optical filter 5, stacked on top of substrate 1 to control the spectrum of the emitted/detected IR radiation. The chemical sensing device further comprises a semiconductor substrate 6, stacked on top of the optical filter 5, to form the fluid cell (or chamber) through which IR radiation propagates. The fluid cell (or the chamber) is formed by a cavity created using a wet etching process resulting in sloping side-walls. The dielectric layer 7 acts as etch-stop. The cavity is used to channel IR radiation from the source to the detector and through the fluid ($CO_2$, in this specific case). A reflective layer(s) 8 on the walls of the cavity is used to improve the side-walls reflectivity and thus to reduce optical losses.

Figure 2:
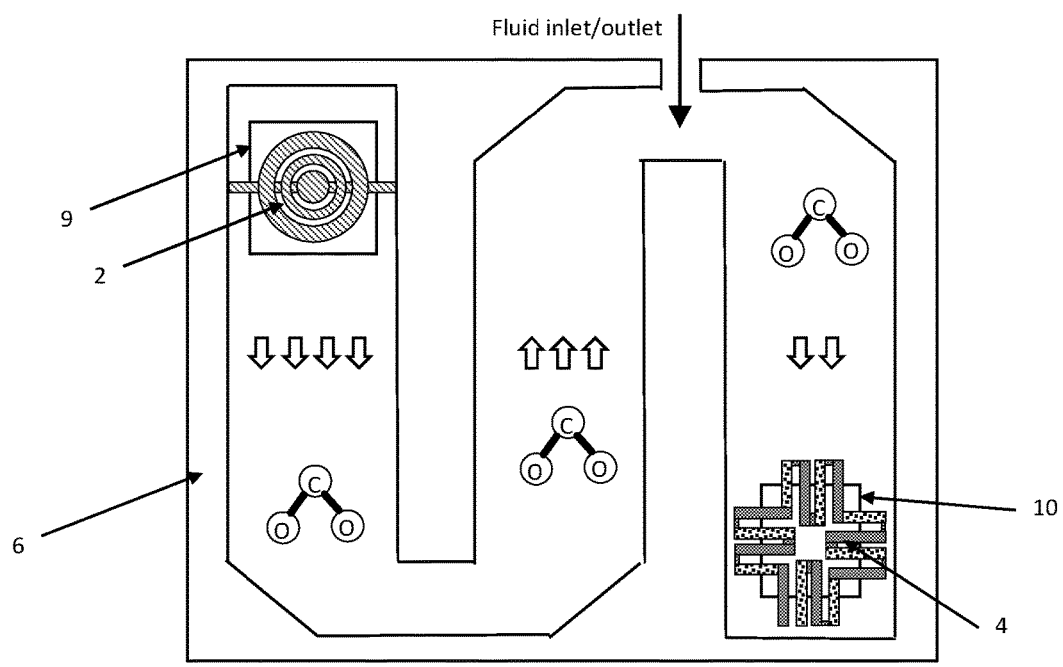
FIG. 2 is a top view of a chip level NDIR chemical sensor having a fluid cell with meander shape.

FIG. 2 shows the top view of chemical sensing device, comprising an IR source and an IR detector fabricated on the same semiconductor substrate 1. The IR source is in form of an electrically resistive heater 2, embedded within a membrane 9 formed by etching the semiconductor substrate 1. The IR detector is in form of a thermopile 4, embedded within a membrane 10 formed by etching the semiconductor substrate 1. The chemical sensing device further comprises a semiconductor substrate 6 to form the fluid cell through which IR radiation propagates. The fluid cell (chamber) is formed by a cavity created using a semiconductor etching process. The cavity is used to channel IR radiation from the source to the detector and through the fluid ($CO_2$, in this specific case). Furthermore a fluid inlet/outlet is provided. It should be obvious that this is only one possible shape for the optical path and that many other shapes are possible such a spiral, ring, or a meander shape with many different bends etc. Furthermore there can be several fluid inlets and outlets within the path.

Figure 3:
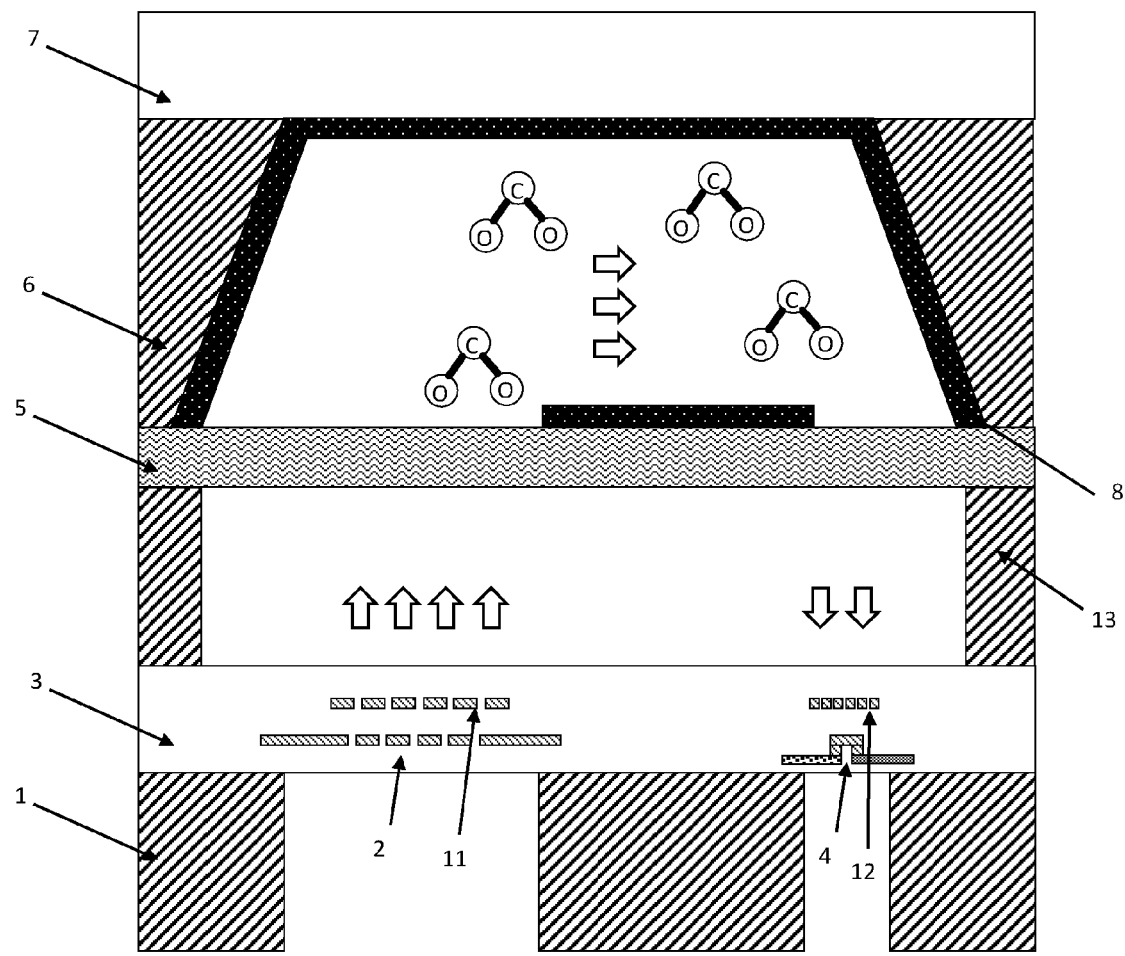
FIG. 3 is a cross sectional view of a chip level NDIR chemical sensor with a spacer between the IR devices and the optical filter.

FIG. 3 shows the cross-section of a chemical sensing device, comprising an IR source and an IR detector fabricated on the same semiconductor substrate 1. The IR source is in form of an electrically resistive heater 2, embedded within a membrane formed by etching the semiconductor substrate 1. The dielectric layer 3 acts as etch-stop. A plasmonic layer 11 is also embedded within the membrane, to tailor the emission properties of the IR emitter. The IR detector is in form of a thermopile 4, embedded within a membrane formed by etching the semiconductor substrate 1. The dielectric layer 3 acts as etch-stop. A plasmonic layer 12 is also embedded within the membrane, to tailor the absorption properties of the IR detector. The chemical sensing device further comprises an optical filter 5, stacked on top of substrate 13, to control the spectrum of the emitted/detected IR radiation. The chemical sensing device further comprises a semiconductor substrate 6, stacked on top of the optical filter 5, to form the fluid cell through which IR radiation propagates. The fluid cell (chamber) is formed by a cavity created using a wet etching process resulting in sloping side-walls. The dielectric layer 7 acts as etch-stop. The cavity is used to channel IR radiation from the source to the detector and through the fluid ($CO_2$, in this specific case). A reflective layer(s) 8 on the walls of the cavity is used to improve the side-walls reflectivity and thus to reduce optical losses.

Figure 4:
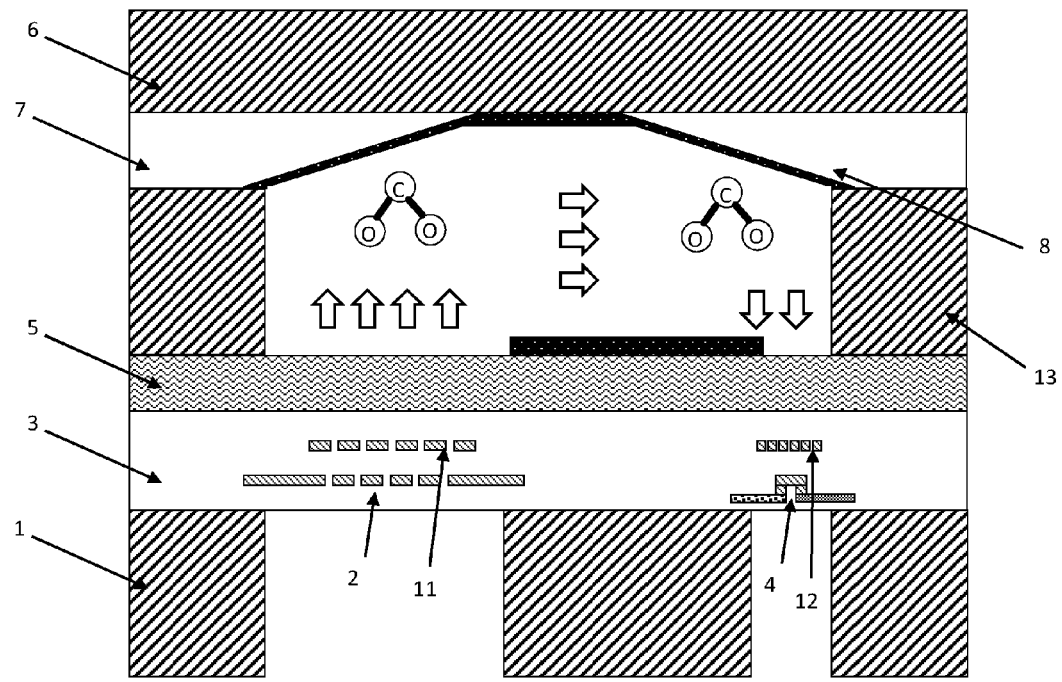
FIG. 4 is a cross sectional view of a chip level NDIR chemical sensor having the substrate forming the fluid cell (chamber) front etched.

FIG. 4 shows the cross-section of a chemical sensing device, comprising an IR source and an IR detector fabricated on the same semiconductor substrate 1. The IR source is in form of an electrically resistive heater 2, embedded within a membrane formed by etching the semiconductor substrate 1. The dielectric layer 3 acts as etch-stop. A plasmonic layer 11 is also embedded within the membrane, to tailor the emission properties of the IR emitter. The IR detector is in form of a thermopile 4, embedded within a membrane formed by etching the semiconductor substrate 1. The dielectric layer 3 acts as etch-stop. A plasmonic layer 12 is also embedded within the membrane, to tailor the absorption properties of the IR detector. The chemical sensing device further comprises an optical filter 5, stacked on top of substrate 1, to control the spectrum of the emitted/detected IR radiation. The chemical sensing device further comprises a semiconductor substrate 13 and a semiconductor substrate 6, stacked on top of the optical filter 5, to form the fluid cell through which IR radiation propagates. The fluid cell (chamber) is formed by a cavity created using substrate 13 as spacer and by front wet etching the dielectric layer 7, resulting in sloping side-walls. The semiconductor substrate 6 acts as front etch-stop. The cavity is used to channel IR radiation from the source to the detector and through the fluid ($CO_2$, in this specific case). A reflective layer(s) 8 on the walls of the cavity is used to improve the side-walls reflectivity and thus to reduce optical losses.

Figure 5:
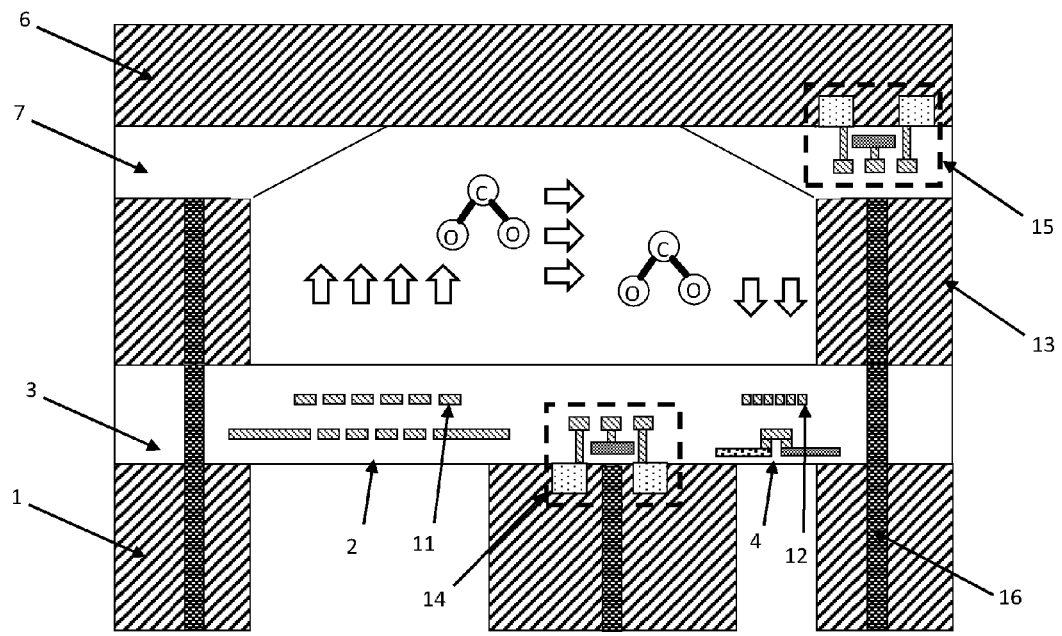
FIG. 5 is a cross sectional view of a chip level NDIR chemical sensor with circuitry integrated on-chip and TSVs.

FIG. 5 shows the cross-section of a chemical sensing device, comprising an IR source and an IR detector fabricated on the same semiconductor substrate 1. The IR source is in form of an electrically resistive heater 2, embedded within a membrane formed by etching the semiconductor substrate 1. The dielectric layer 3 acts as etch-stop. A plasmonic layer 11 is also embedded within the membrane, to tailor the emission properties of the IR emitter. The IR detector is in form of a thermopile 4, embedded within a membrane formed by etching the semiconductor substrate 1. The dielectric layer 3 acts as etch-stop. A plasmonic layer 12 is also embedded within the membrane, to tailor the absorption properties of the IR detector. The chemical sensing device further comprises a semiconductor substrate 13 and a semiconductor substrate 6, stacked on top of the semiconductor substrate 1, to form the fluid cell through which IR radiation propagates. The fluid cell (chamber) is formed by a cavity created using substrate 13 as spacer and by front wet etching the dielectric layer 7, resulting in sloping side-walls. The semiconductor substrate 6 acts as front etch-stop. The cavity is used to channel IR radiation from the source to the detector and through the fluid ($CO_2$, in this specific case). The chemical sensing device further comprises some electronics schematically represented by FET 14 and by FET 15. FET 14 is integrated on the semiconductor substrate 1. FET 15 is integrated on the semiconductor substrate 6. FET 14 and FET 15 are realised using different CMOS technology nodes (e.g. FET 14 using a 1 μm semiconductor process technology and FET 15 using a 180 nm process). Through Silicon Via (TSV) technology 16 is also used to facilitate connections between different substrates and reduce the chemical sensing device form factor.

Figure 6:
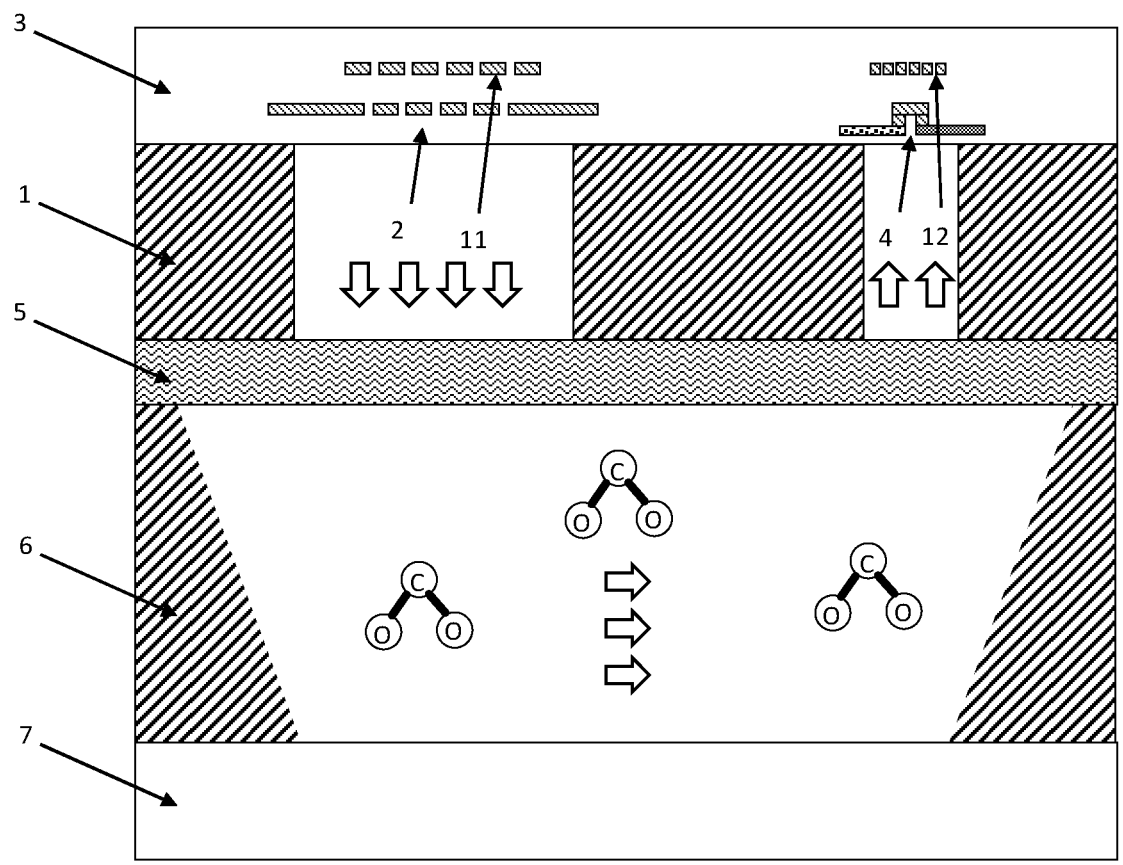
FIG. 6 is a cross sectional view of a chip level NDIR chemical sensor wherein radiation is emitted and detected from the bottom of the IR devices.

FIG. 6 shows the cross-section of a chemical sensing device, comprising an IR source and an IR detector fabricated on the same semiconductor substrate 1. The IR source is in form of an electrically resistive heater 2, embedded within a membrane formed by etching the semiconductor substrate 1. The dielectric layer 3 acts as etch-stop. A plasmonic layer (or the patterned structures) 11 is also embedded within the membrane, to tailor the emission properties of the IR emitter. The IR detector is in form of a thermopile 4, embedded within a membrane formed by etching the semiconductor substrate 1. The dielectric layer 3 acts as etch-stop. A plasmonic layer (or the patterned structures) 12 is also embedded within the membrane, to tailor the absorption properties of the IR detector. The chemical sensing device further comprises an optical filter 5, stacked underneath substrate 1 to control the spectrum of the bottom emitted/detected IR radiation. The chemical sensing device further comprises a semiconductor substrate 6, stacked underneath the optical filter 5, to form the fluid cell through which IR radiation propagates. The fluid cell is formed by a cavity created using a wet etching process resulting in sloping side-walls. The dielectric layer 7 acts as etch-stop. The cavity is used to channel IR radiation from the source to the detector and through the fluid ($CO_2$, in this specific case).

Figure 7:
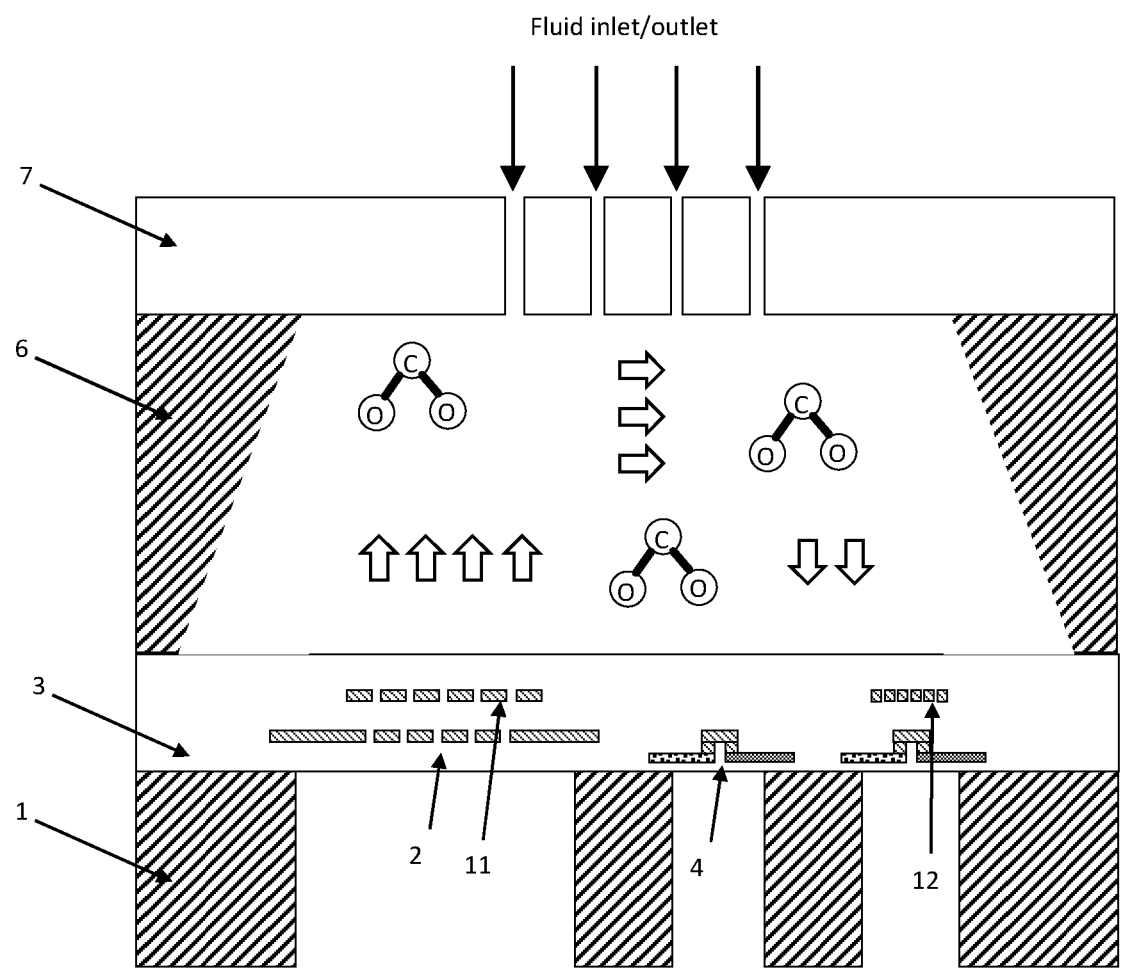
FIG. 7 is a cross sectional view of a chip level NDIR chemical sensor having plasmonic differential read-out and showing fluid inlet/outlet(s) etched in the topmost substrate.

FIG. 7 shows the cross-section of a chemical sensing device, comprising an IR source and an IR detector array (two detectors in this specific case) fabricated on the same semiconductor substrate 1. The IR source is in form of an electrically resistive heater 2, embedded within a membrane formed by etching the semiconductor substrate 1. The dielectric layer 3 acts as etch-stop. A plasmonic layer (or the patterned structures) 11 is also embedded within the membrane, to tailor the emission properties of the IR emitter. The IR detector array is in form of thermopiles 4, embedded within different membranes formed by etching the semiconductor substrate 1. The dielectric layer 3 acts as etch-stop. A plasmonic layer (or the patterned structures) 12 is also embedded within the membrane of one of the IR detectors, to tailor the absorption properties of that specific IR detector. The chemical sensing device further comprises a semiconductor substrate 6, stacked on top of the semiconductor substrate 1, to form the fluid cell through which IR radiation propagates. The fluid cell is formed by a cavity created using substrate by wet etching the semiconductor substrate 6, resulting in sloping side-walls. The dielectric layer 7 acts as etch-stop. The cavity is used to channel IR radiation from the source to the detector and through the fluid ($CO_2$, in this specific case). Furthermore fluid inlet/outlet are provided. The detection takes place by looking at the differential signal resulting from the two thermopiles forming the IR detector array. Alternately both the IR detectors can have a plasmonic layer, but optimized for different wavelengths. There can also be more than two IR detectors each of which has either different types of plasmonic layers, same plasmonic layers, or no plasmonic layer.

Figure 8:
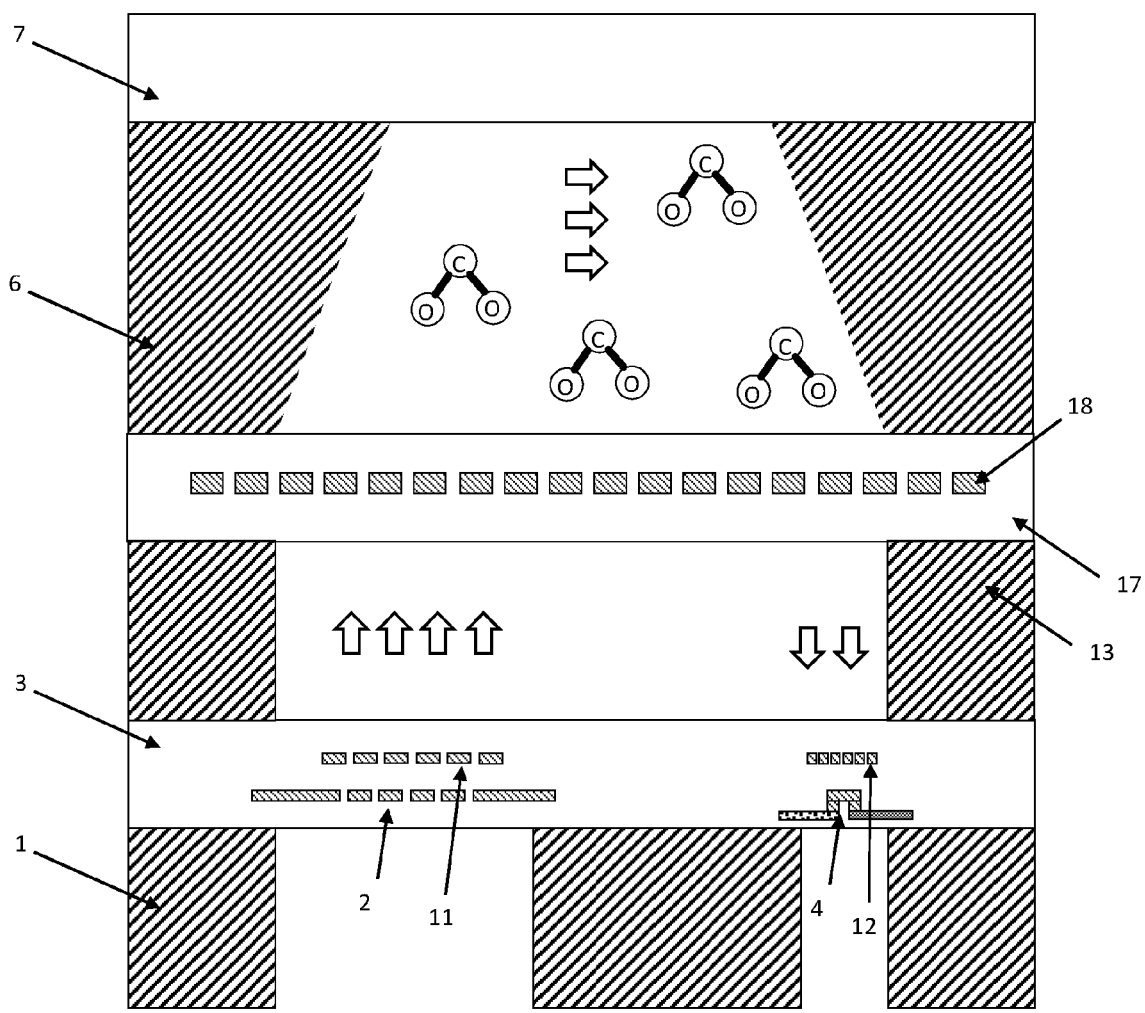
FIG. 8 is a cross sectional view of a chip level NDIR chemical sensor having a plasmonic optical filter.

FIG. 8 shows the cross-section of a chemical sensing device, comprising an IR source and an IR detector fabricated on the same semiconductor substrate 1. The IR source is in form of an electrically resistive heater 2, embedded within a membrane formed by etching the semiconductor substrate 1. The dielectric layer 3 acts as etch-stop. A plasmonic layer (or the patterned structures) 11 is also embedded within the membrane, to tailor the emission properties of the IR emitter. The IR detector is in form of a thermopile 4, embedded within a membrane formed by etching the semiconductor substrate 1. The dielectric layer 3 acts as etch-stop. A plasmonic layer 12 is also embedded within the membrane, to tailor the absorption properties of the IR detector. The chemical sensing device further comprises a semiconductor substrate 13, which is etched to form a membrane, and acts as optical filter stacked on top of substrate 1. The dielectric layer 17 acts as etch-stop. A plasmonic layer (or the patterned structures) 18 is embedded within the dielectric layer 17, to further control the spectrum of the emitted/detected IR radiation. The chemical sensing device further comprises a semiconductor substrate 6, stacked on top of the semiconductor substrate 13, to form the fluid cell through which IR radiation propagates. The fluid cell is formed by a cavity created using a wet etching process resulting in sloping side-walls. The dielectric layer 7 acts as etch-stop. The cavity is used to channel IR radiation from the source to the detector and through the fluid ($CO_2$, in this specific case).

Figure 9:
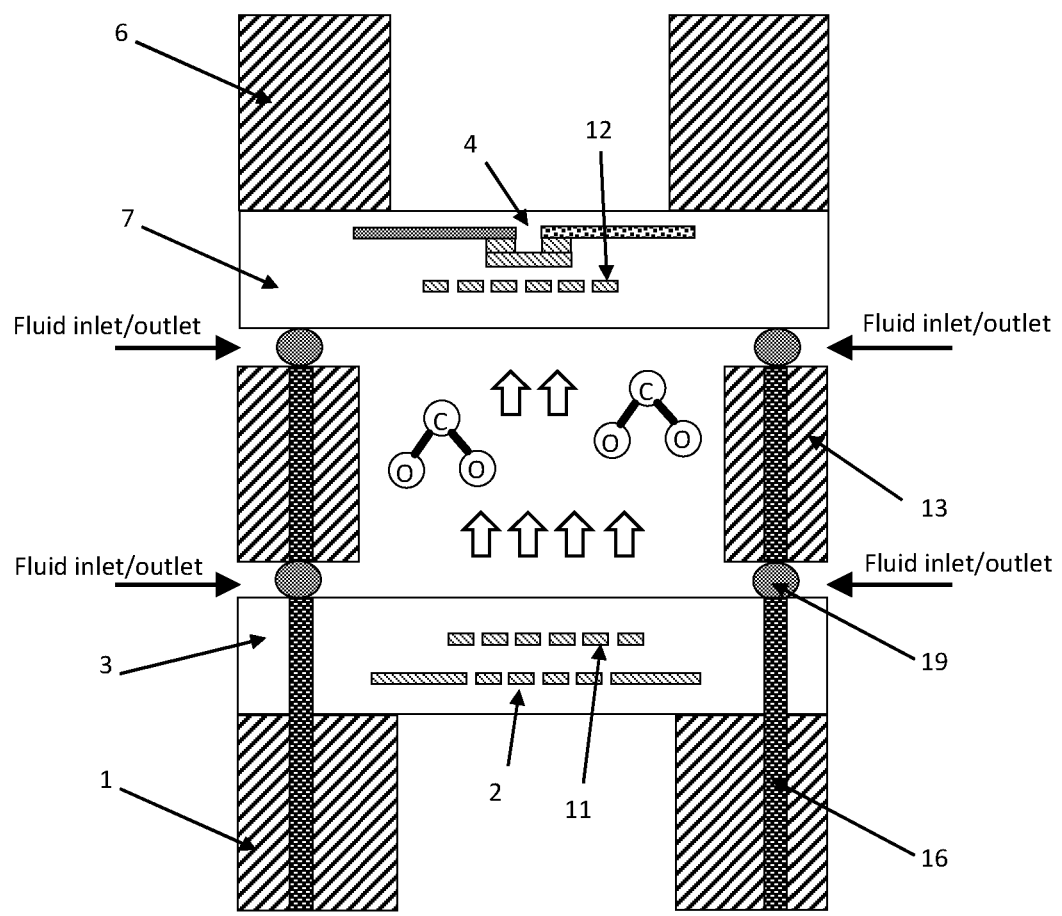
FIG. 9 is a cross sectional view of a chip level NDIR chemical sensor wherein IR emitter and IR detector face each other and are assembled by solder balls and flip-chip method.

FIG. 9 shows the cross-section of a chemical sensing device, comprising an IR source fabricated on the semiconductor substrate 1. The IR source is in form of an electrically resistive heater 2, embedded within a membrane formed by etching the semiconductor substrate 1. The dielectric layer 3 acts as etch-stop. A plasmonic layer (or the patterned structures) 11 is also embedded within the membrane, to tailor the emission properties of the IR emitter. The chemical sensing device further comprises a semiconductor substrate 13, stacked on top of substrate 1. The chemical sensing device further comprises an IR detector fabricated on the semiconductor substrate 6, stacked on top of substrate 13 via flip-chip method. The IR detector is in form of a thermopile 4, embedded within a membrane formed by etching the semiconductor substrate 6. The dielectric layer 7 acts as etch-stop. A plasmonic layer (or the patterned structures) 12 is also embedded within the membrane, to tailor the absorption properties of the IR detector. The semiconductor substrates 1, 6 and 13 are joint together via ball bonds 19. Advantageously, this method results in a spacing between the substrates which act as fluid inlet/outlet.

Figure 10:
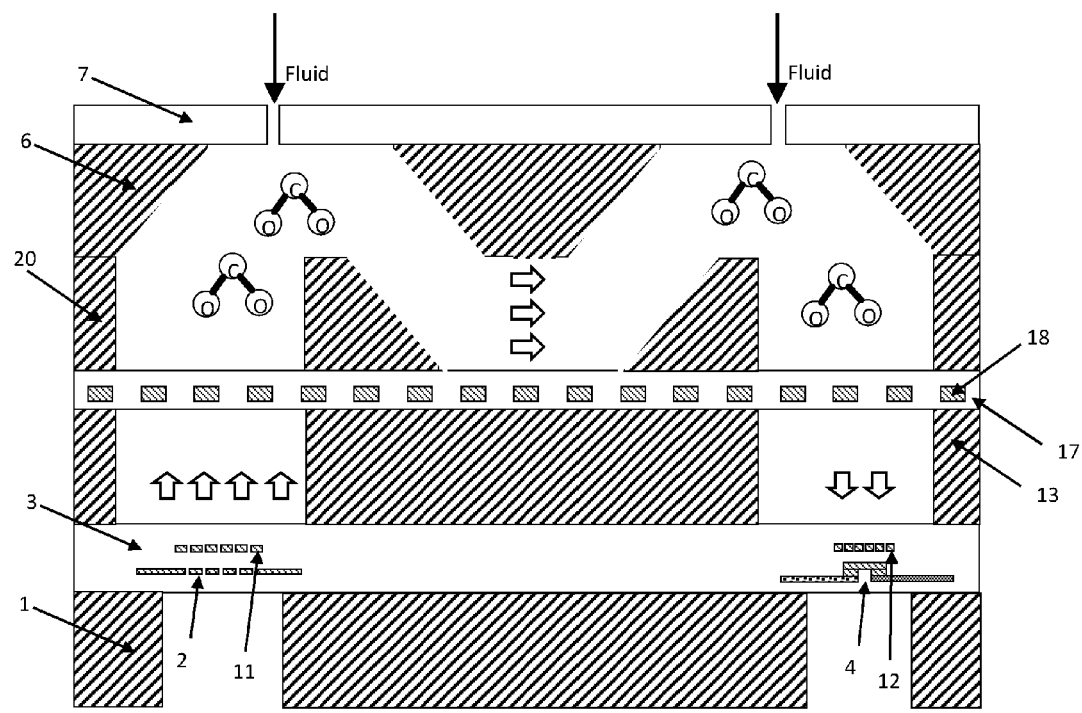
FIG. 10 is a cross sectional view of a chip level NDIR chemical sensor with cross sectional meander shape.

FIG. 10 shows the cross-section of a chemical sensing device, comprising an IR source and an IR detector fabricated on the same semiconductor substrate 1. The IR source is in form of an electrically resistive heater 2, embedded within a membrane formed by etching the semiconductor substrate 1. The dielectric layer 3 acts as etch-stop. A plasmonic layer (or the patterned structures) 11 is also embedded within the membrane, to tailor the emission properties of the IR emitter. The IR detector is in form of a thermopile 4, embedded within a membrane formed by etching the semiconductor substrate 1. The dielectric layer 3 acts as etch-stop. A plasmonic layer (or the patterned structures) 12 is also embedded within the membrane, to tailor the absorption properties of the IR detector. The chemical sensing device further comprises a semiconductor substrate 13, which is etched to form membranes, and acts as optical filter stacked on top of substrate 1. The dielectric layer 17 acts as etch-stop. A plasmonic layer (or the patterned structures) 18 is embedded within the dielectric layer 17, to further control the spectrum of the emitted/detected IR radiation. The chemical sensing device further comprises semiconductor substrates 20 and 6, stacked on top of the semiconductor substrate 13, to form the fluid cell through which IR radiation propagates. The fluid cell is formed by a cavity created using a wet etching process resulting in sloping side-walls. The dielectric layer 7 acts as etch-stop. The cavity is used to channel IR radiation from the source to the detector and through the fluid ($CO_2$, in this specific case). Furthermore fluid inlet/outlet are provided.

Figure 11:
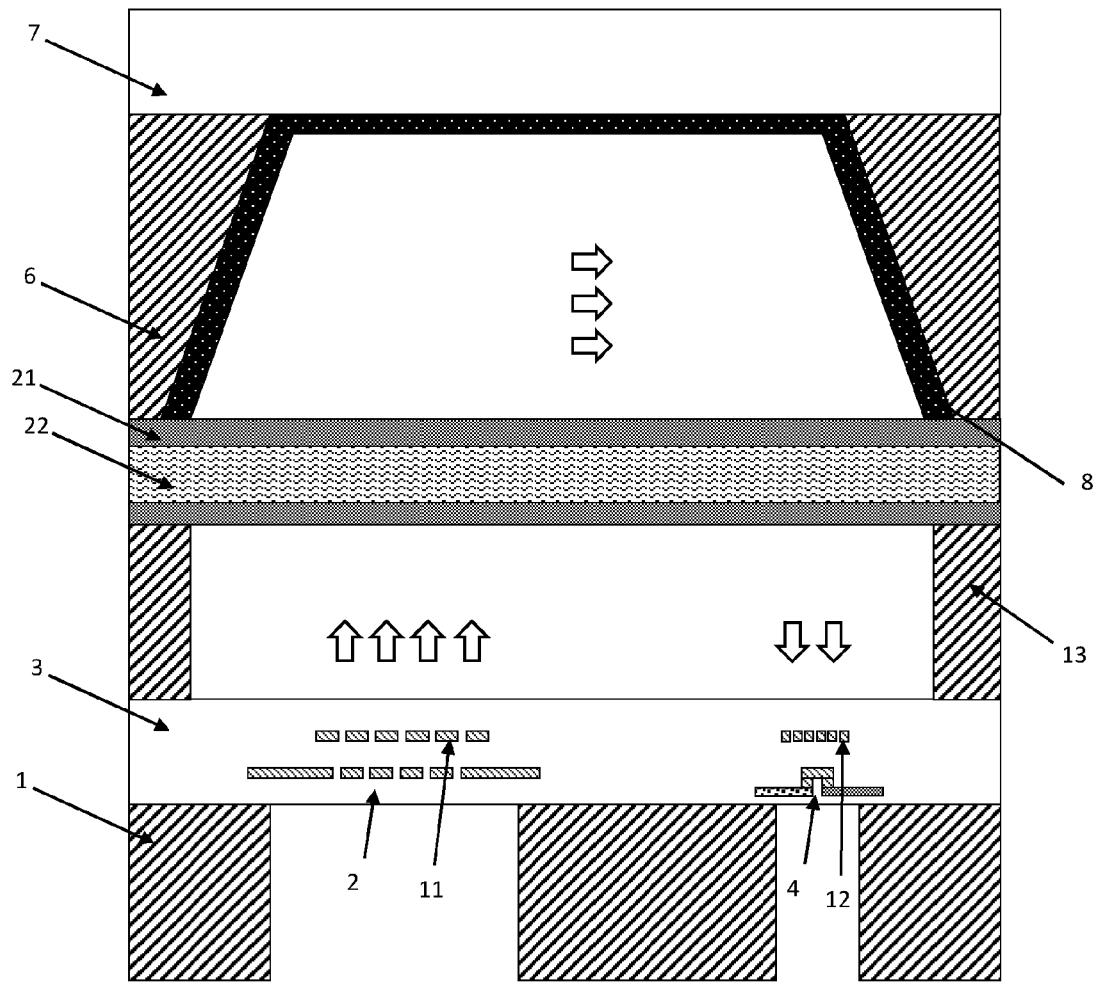
FIG. 11 is a cross sectional view of a chip level NDIR chemical sensor co-integrated with a microfluidic channel.

FIG. 11 shows the cross-section of a chemical sensing device, comprising an IR source and an IR detector fabricated on the same semiconductor substrate 1. The IR source is in form of an electrically resistive heater 2, embedded within a membrane formed by etching the semiconductor substrate 1. The dielectric layer 3 acts as etch-stop. A plasmonic layer 11 is also embedded within the membrane, to tailor the emission properties of the IR emitter. The IR detector is in form of a thermopile 4, embedded within a membrane formed by etching the semiconductor substrate 1. The dielectric layer 3 acts as etch-stop. A plasmonic layer 12 is also embedded within the membrane, to tailor the absorption properties of the IR detector. The chemical sensing device further comprises a microfluidic channel 21, stacked on top of substrate 13, to allow interaction of the fluid under test 22 with the emitted IR radiation. The chemical sensing device further comprises a semiconductor substrate 6, stacked on top of the microfluidic channel 21, to form the fluid cell through which IR radiation propagates. The fluid cell is formed by a cavity created using a wet etching process resulting in sloping side-walls. The dielectric layer 7 acts as etch-stop. The cavity is used to channel IR radiation from the source to the detector and through the fluid under test 22. A reflective layer(s) 8 on the walls of the cavity is used to improve the side-walls reflectivity and thus to reduce optical losses.

Figure 12:
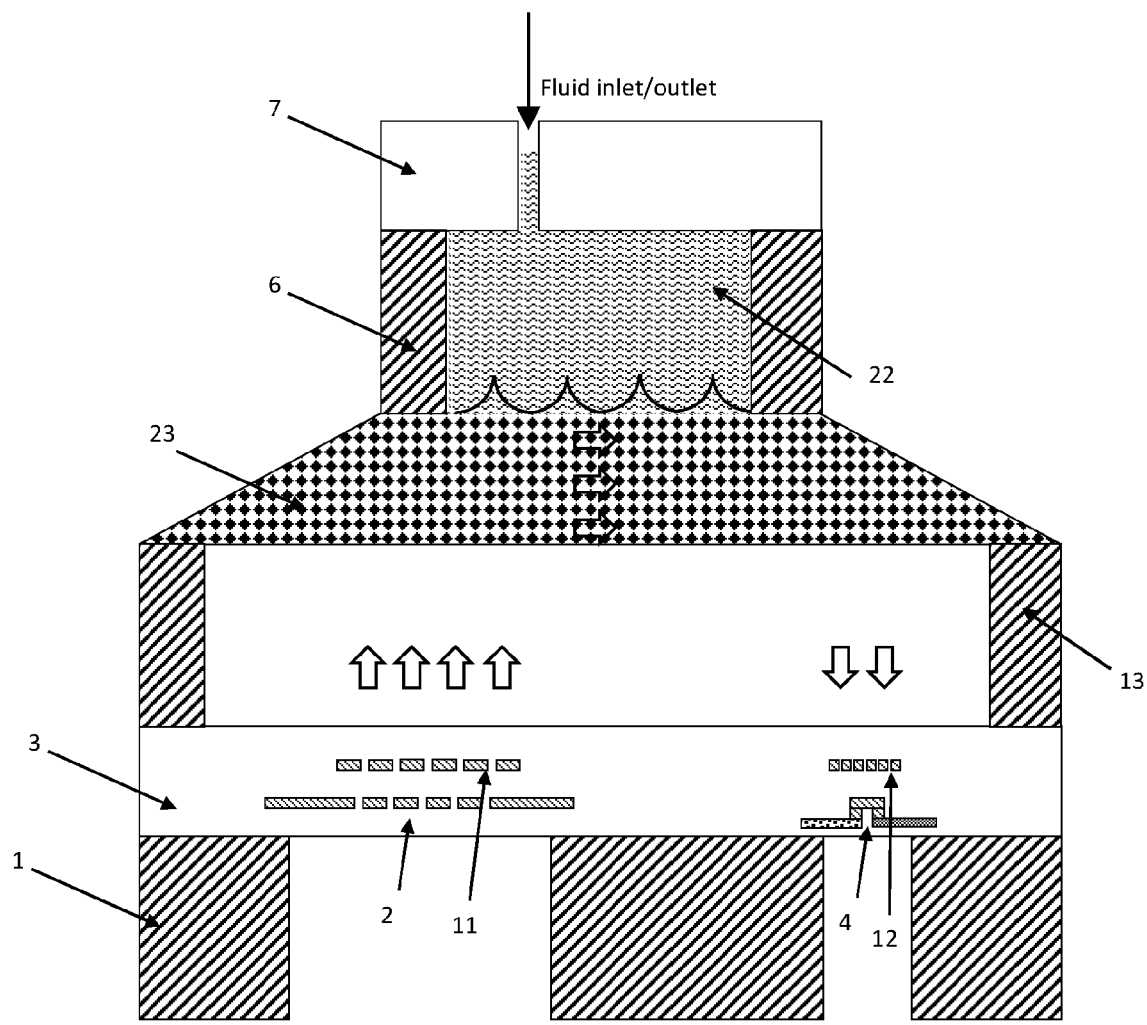
FIG. 12 is a cross sectional view of a chip level NDIR chemical sensor in ATR configuration.

FIG. 12 shows the cross-section of a chemical sensing device, comprising an IR source and an IR detector fabricated on the same semiconductor substrate 1. The IR source is in form of an electrically resistive heater 2, embedded within a membrane formed by etching the semiconductor substrate 1. The dielectric layer 3 acts as etch-stop. A plasmonic layer 11 is also embedded within the membrane, to tailor the emission properties of the IR emitter. The IR detector is in form of a thermopile 4, embedded within a membrane formed by etching the semiconductor substrate 1. The dielectric layer 3 acts as etch-stop. A plasmonic layer 12 is also embedded within the membrane, to tailor the absorption properties of the IR detector. The chemical sensing device further comprises a substrate 23, stacked on top of substrate 13, which channels IR radiation from the IR source to the IR detector. Evanescent waves, created by the reflections internal to the substrate 23, interact with the fluid 22. A further etched semiconductor substrate 6 is stacked on top of the substrate 23 to form a fluid reservoir. The dielectric layer 7 acts as etch-stop. A fluid inlet/outlet is also provided.

Figure 13:
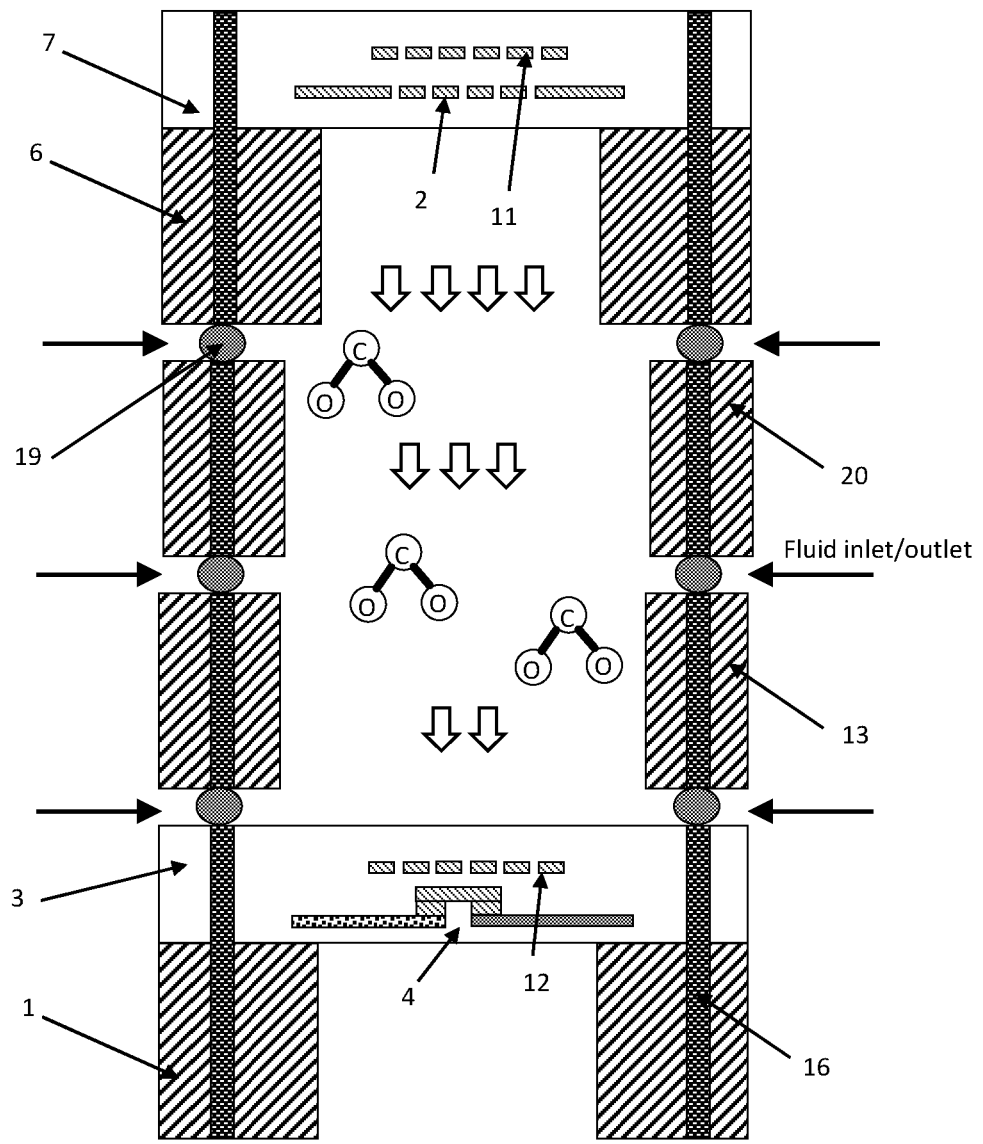
FIG. 13 is a cross sectional view of a chip level NDIR chemical sensor with vertical straight through optical path.

FIG. 13 shows the cross-section of a chemical sensing device, comprising an IR detector fabricated on the semiconductor substrate 1. The IR detector is in form of a thermopile 4, embedded within a membrane formed by etching the semiconductor substrate 1. The dielectric layer 3 acts as etch-stop. A plasmonic layer 12 is also embedded within the membrane, to tailor the absorption properties of the IR detector. The chemical sensing device further comprises a semiconductor substrate 13 and a semiconductor substrate 20, stacked on top of substrate 1. The chemical sensing device further comprises an IR source fabricated on the semiconductor substrate 6. The IR source is in form of an electrically resistive heater 2, embedded within a membrane formed by etching the semiconductor substrate 6. The dielectric layer 7 acts as etch-stop. A plasmonic layer 11 is also embedded within the membrane, to tailor the emission properties of the IR emitter. The semiconductor substrates 1, 6, 13 and 20 are joint together via ball bonds 19. Advantageously, this method results in a spacing between the substrates which acts as fluid inlet/outlet. Through Silicon Via (TSV) technology 16 is also used to facilitate connections between different substrates and reduce the chemical sensing device form factor.

Figure 14:
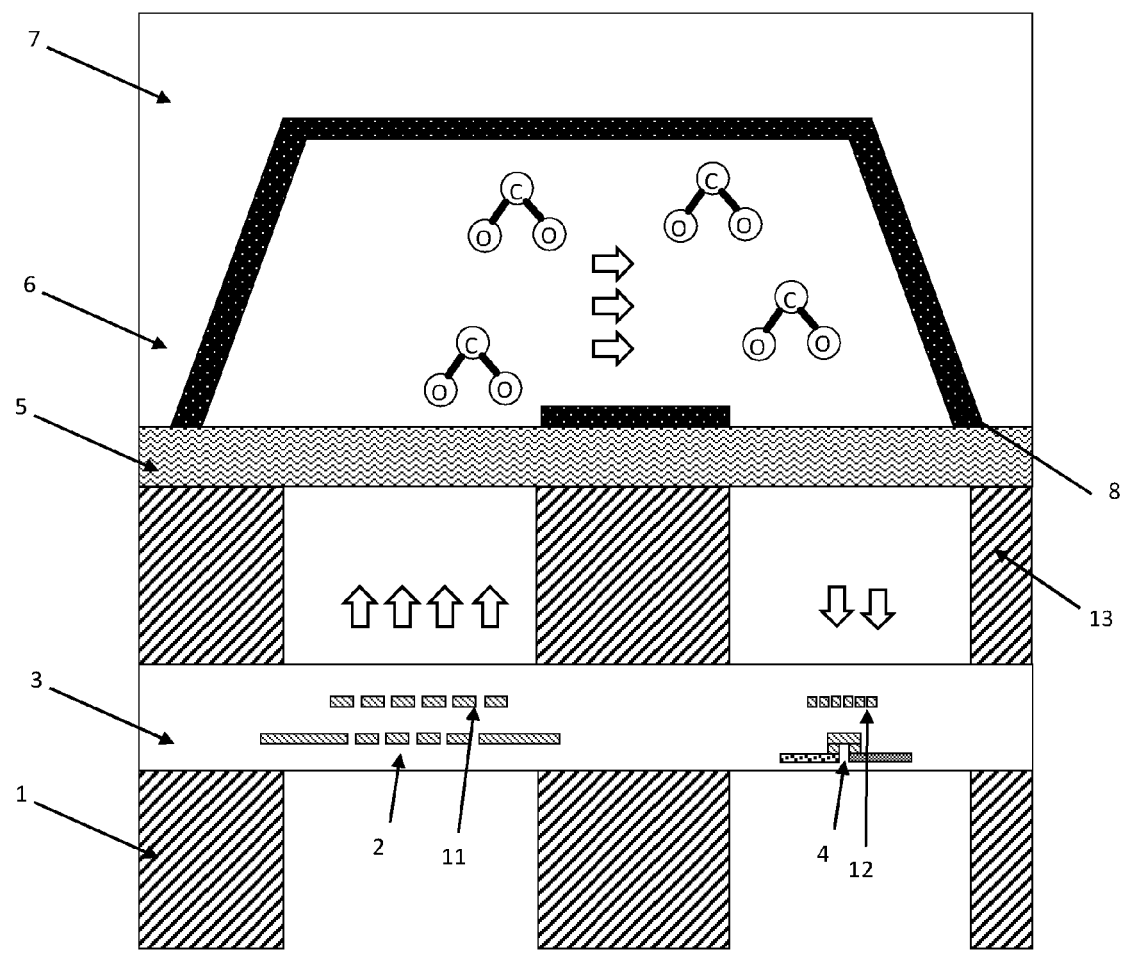
FIG. 14 is an alternative cross sectional view of a chip level NDIR chemical sensor.

FIG. 14 shows the cross-section of a chemical sensing device, comprising an IR source and an IR detector fabricated on the same semiconductor substrate 1. The IR source is in form of an electrically resistive heater 2, embedded within a membrane formed by etching the semiconductor substrate 1. The dielectric layer 3 acts as etch-stop. A plasmonic layer 11 is also embedded within the membrane, to tailor the emission properties of the IR emitter. The IR detector is in form of a thermopile 4, embedded within a membrane formed by etching the semiconductor substrate 1. The dielectric layer 3 acts as etch-stop. A plasmonic layer 12 is also embedded within the membrane, to tailor the absorption properties of the IR detector. The chemical sensing device further comprises an optical filter 5, stacked on top of substrate 13, to control the spectrum of the emitted/detected IR radiation. The chemical sensing device further comprises a semiconductor substrate 6, stacked on top of the optical filter 5, to form the fluid cell through which IR radiation propagates. The fluid cell is formed by a cavity created using a timed wet etching process resulting in sloping side-walls. The cavity is used to channel IR radiation from the source to the detector and through the fluid ($CO_2$, in this specific case). A reflective layer(s) 8 on the walls of the cavity is used to improve the side-walls reflectivity and thus to reduce optical losses.

Figures 15A, 15B:
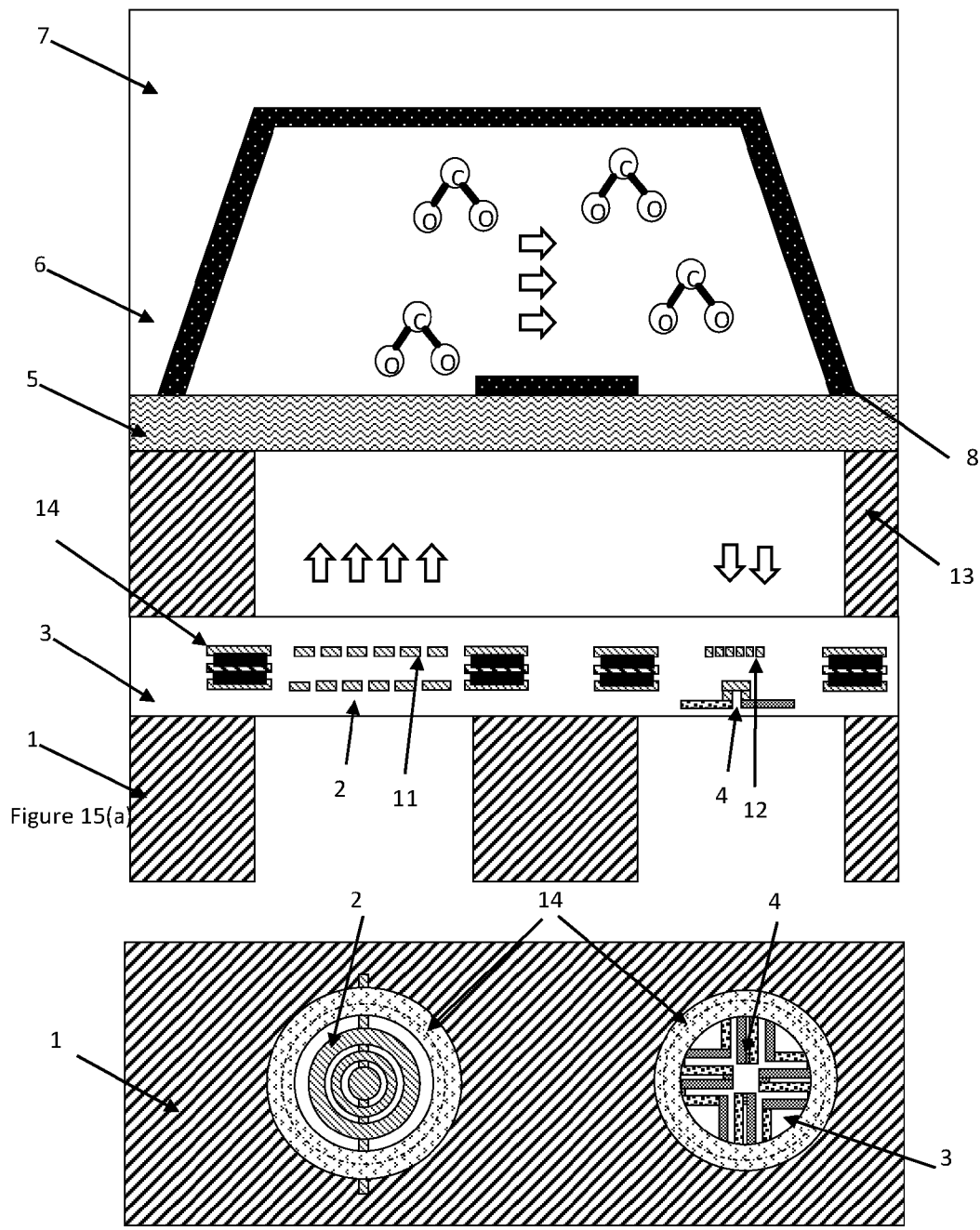
FIG. 15($a$) shows the cross-section of a chemical sensing device, comprising an IR source and an IR detector fabricated on the same semiconductor substrate.

FIG. 15(*a*) shows the cross-section of a chemical sensing device, comprising an IR source and an IR detector fabricated on the same semiconductor substrate 1. The IR source is in form of an electrically resistive heater 2, embedded within a membrane formed by etching the semiconductor substrate 1. The dielectric layer 3 acts as etch-stop. A plasmonic layer 11 is also embedded within the membrane, to tailor the emission properties of the IR emitter. The IR detector is in form of a thermopile 4, embedded within a membrane formed by etching the semiconductor substrate 1. The dielectric layer 3 acts as etch-stop. A plasmonic layer 12 is also embedded within the membrane, to tailor the absorption properties of the IR detector. The resistive heater 2 of the IR emitter and the thermopile 4 of the IR detector is enclosed a metal rings 14 that overlaps etched and un-etched part of the substrate. The ring will provide good thermal isolation between emitter and detectors and reduce the effects of etch tolerance variations. Similarly, ring structures can also be added to stacked substrate 13 and any other stacked embodiments as described in the previous figures.

FIG. 15(*b*) shows top view of the embodiment of the ring structures 14, that overlaps the etched and un-etched parts of the substrate.

Figure 16:
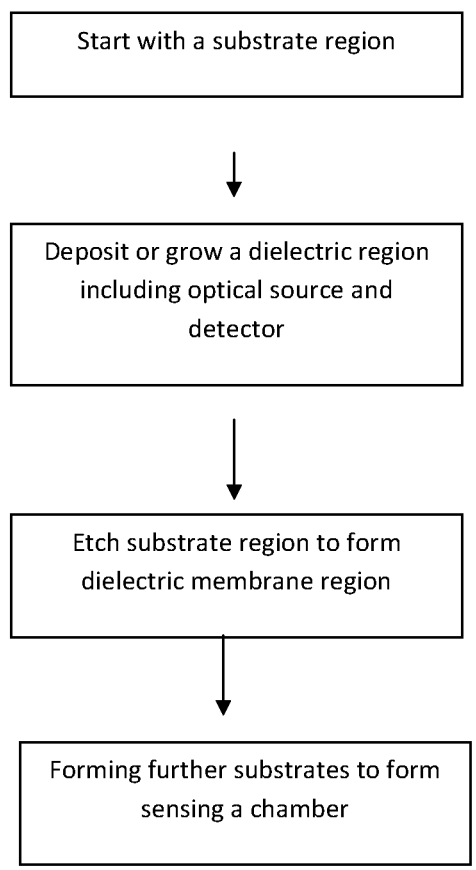
FIG. 16 is a flow diagram including manufacturing steps of the NDIR chemical sensor.

FIG. 16 is a flow diagram including manufacturing steps of the NDIR chemical sensor.

The skilled person will understand that in the preceding description and appended claims, positional terms such as 'above', 'below', 'front', 'back', 'vertical', 'underneath' etc. are made with reference to conceptual illustrations of a semiconductor device, such as those showing standard cross-sectional perspectives and those shown in the appended drawings. These terms are used for ease of reference but are not intended to be of limiting nature. These terms are therefore to be understood as referring to a semiconductor device when in an orientation as shown in the accompanying drawings.

Although the invention has been described in terms of preferred embodiments as set forth above, it should be understood that these embodiments are illustrative only and that the claims are not limited to those embodiments. Those skilled in the art will be able to make modifications and alternatives in view of the disclosure which are contemplated as falling within the scope of the appended claims. Each feature disclosed or illustrated in the present specification may be incorporated in the invention, whether alone or in any appropriate combination with any other feature disclosed or illustrated herein.

The invention claimed is:

1. A chemical sensing device for detecting a fluid, the sensing device comprising:
    at least one semiconductor substrate region comprising at least one etched portion;
    a dielectric region formed on the at least one substrate region, wherein the dielectric region comprises at least one dielectric membrane region immediately adjacent to the at least one etched portion so that no substrate portion is located immediately above and below the dielectric membrane region;
    an optical source for emitting an infra-red (IR) signal;
    an optical detector for detecting the IR signal emitted from the optical source;
    one or more further substrates formed on or under the dielectric region, wherein said one or more further substrates define an optical path for the IR signal to propagate from the optical source to the optical detector; and
    wherein at least one of the optical source and optical detector is formed at least partially in or on the dielectric membrane region.

2. A sensing device according to claim 1, wherein said at least one substrate region comprises a first etched portion and a second etched portion, and
    wherein the dielectric region comprises a first dielectric membrane region adjacent to the first etched portion and a second dielectric membrane region adjacent to the second etched portion, and
    wherein the optical source is located within the first dielectric membrane region and the optical detector is located within the second dielectric membrane region.

3. A sensing device according to claim 2, wherein the optical source and optical detector are laterally spaced to one another.

4. A sensing device according to claim 1, wherein said at least one substrate region comprises a first substrate and a second substrate,
    wherein the first substrate comprises a first etched portion and a first dielectric membrane region is formed adjacent to the first etched portion, and
    wherein the second substrate comprises a second etched portion and a second dielectric membrane region is formed adjacent to the second etched portion, and
    wherein the optical source is located within the first dielectric membrane region and the optical detector is located within the second dielectric membrane region.

5. A sensing device according to claim 4, wherein the optical source and the optical detector are vertically spaced to one another and wherein the one or more further substrates are vertically spaced between the first and second dielectric membrane regions.

6. A sensing device according to claim 1, wherein said one or more further substrates each comprising an etched portion.

7. A sensing device according to claim 6, further comprising a fluid chamber which is formed from said at least one etch portion of said one or more further substrates.

8. A sensing device according to claim 7, wherein the fluid chamber comprises a reflective layer at least partially along a perimeter of the fluid chamber, and wherein the reflective layer comprises a material comprising gold, aluminium, copper, silver and/or platinum.

9. A sensing device according to claim 7, wherein the fluid chamber comprises a fluid hollow channel for a targeted fluid to enter or exit the fluid chamber.

10. A sensing device according to claim 7, wherein the fluid chamber has a spiral, meander, or any other geometric shape which enables the IR signal to propagate from the optical source to the optical detector.

11. A sensing device according to claim 7, further comprising a micro-fluidic channel between the dielectric layer and the fluid chamber for a targeted liquid to flow through the micro-fluidic channel.

12. A sensing device according to claim 1, wherein the one or more further substrates are spaced from the dielectric region to form an opening for a targeted fluid to enter or exit the sensing device.

13. A sensing device according to claim 12, further comprising a ball bond in the opening between the dielectric region and the one or more further substrates.

14. A sensing device according to claim 1, wherein the sensing device is configured to sense a fluid using an attenuated total reflection technique such that one side of one layer of the one or more further substrates receives and transmits the IR signal and propagates the IR signal through said one layer by a total internal reflection or as an evanescent wave that is affected by the fluid on an opposite side of said one layer.

15. A sensing device according to claim 1, further comprising an optical filter between the one or more further substrates and the dielectric region.

16. A sensing device according to claim 1, further comprising one or more layers of patterned structures within the dielectric membrane, wherein some of said patterned structures are over or under the optical source, and wherein some other of said patterned structures are over or under the optical detector.

17. A sensing device according to claim 1, comprising a further dielectric region between two further substrates over the dielectric membrane, and wherein the further dielectric region comprises a layer of patterned structures to control a spectrum of the IR signal propagating between the optical source and optical detector.

18. A sensing device according to claim 1, wherein the one or more further substrates are coupled with the dielectric region comprising the dielectric membrane region using one or more of the following techniques:
a plurality of ball bonds;
solder pads;
bump bonding;
adhesive bonding;
thermo-compression;
direct bonding;
wafer bonding; and/or
a hybrid technique.

19. A sensing device according to claim 1, further comprising through silicon vias (TSVs) in the substrate region, the dielectric region and the one or more further substrates, wherein the TSVs are configured to provide electrical connections to an external system or between substrates.

20. A sensing device according to claim 1, further comprising circuitry integrated in the substrate region and in the one or more further substrates.

21. A sensing device according to claim 1, wherein the substrate region and the one or more further substrates each comprise a CMOS technology node.

22. A sensing device according to claim 1, wherein the optical source comprises a resistive heater formed using a CMOS technique or a non-CMOS technique.

23. A sensing device according to claim 1, wherein the optical source is a quantum source comprising a light emitting diode (LED) or a laser device.

24. A sensing device according to claim 1, wherein the optical detector is a thermal detector comprising a thermopile, a bolometer or a pyroelectric detector.

25. A sensing device according to claim 1, wherein the optical detector is a quantum detector comprising a photodiode or a photoconductive detector.

26. A sensing device according to claim 1, wherein the device is packaged using one or more of:
a metal transistor output (TO) type package;
a ceramic, metal or plastic surface mount package;
IR filters;
a reflector;
a flip-chip method;
a chip or wafer level package;
a lens;
a printed circuitry board (PCB).

27. A sensing device according to claim 26, wherein the substrate region is attached to a package using one or more of the following techniques:
a plurality of ball bonds;
solder pads;
bump bonding;
adhesive bonding;
thermo-compression;
direct bonding;
wafer bonding; and/or
a hybrid technique.

28. A method of manufacturing a chemical sensing device for detecting a fluid, the method comprising:
forming at least one substrate region;
depositing a dielectric region on the at least one substrate region, wherein the dielectric region comprises at least one dielectric membrane region immediately adjacent to the at least one etched portion so that no substrate portion is located immediately above and below the dielectric membrane region;
forming an optical source for emitting an infra-red (IR) signal;
forming an optical detector for detecting the IR signal emitted from the optical source;
etching the at least one substrate region to form an etched portion in the substrate region and at least one dielectric membrane region in the dielectric region, the at least one dielectric membrane region being immediately adjacent to the etched portion;
forming one or more further substrates on or under the dielectric region, wherein said one or more further substrates define an optical path for the IR signal to propagate from the optical source to the optical detector; and
wherein at least one of the optical source and optical detector is formed in or on the dielectric membrane region.

29. A method according to claim 28, wherein said at least one dielectric membrane region and said one or more further substrates are formed by any one of:
back-etching using Deep Reactive Ion Etching (DRIE) of the substrate, which results in vertical sidewalls; and
using anisotropic etching such as KOH (Potassium Hydroxide) or TMAH (Tetra Methyl Ammonium Hydroxide) which results in slopping sidewalls.

30. A method according to claim 28, wherein the chemical sensor is manufactured using CMOS compatible processing steps.

* * * * *